(12) United States Patent
Chuang et al.

(10) Patent No.: US 9,227,899 B2
(45) Date of Patent: Jan. 5, 2016

(54) PROCESS FOR PRODUCING PROPYLENE GLYCOL METHYL ETHER

(71) Applicants: Karl T. Chuang, Edmonton (CA); Christina Dirk-Faitakis, Edmonton (CA)

(72) Inventors: Karl T. Chuang, Edmonton (CA); Christina Dirk-Faitakis, Edmonton (CA)

(73) Assignee: Shiny Chemical Industrial Co., Ltd. (TW)

( * ) Notice: Subject to any disclaimer, the term of this patent is extended or adjusted under 35 U.S.C. 154(b) by 154 days.

(21) Appl. No.: 13/987,699

(22) Filed: Aug. 22, 2013

(65) Prior Publication Data

US 2015/0057468 A1    Feb. 26, 2015

(51) Int. Cl.
  *C07C 41/44*  (2006.01)
  *C07C 41/03*  (2006.01)
  *C07C 41/42*  (2006.01)

(52) U.S. Cl.
  CPC ............. *C07C 41/44* (2013.01); *C07C 41/03* (2013.01); *C07C 41/42* (2013.01)

(58) Field of Classification Search
  CPC .......... C07C 41/03; C07C 41/42; C07C 41/44
  See application file for complete search history.

(56) References Cited

U.S. PATENT DOCUMENTS

| 5,945,568 A * | 8/1999 | Nagata et al. ............. 568/618 |
| 2009/0018370 A1 * | 1/2009 | Fukuoka et al. ........... 568/852 |

FOREIGN PATENT DOCUMENTS

CN    101613259    * 12/2009

OTHER PUBLICATIONS

English translation of CN101613259, Dec. 30, 2009.*

* cited by examiner

*Primary Examiner* — Paul A Zucker
*Assistant Examiner* — Mark Luderer
(74) *Attorney, Agent, or Firm* — George A. Seaby (57) ABSTRACT

Propylene glycol methyl ether is produced by feeding a solution of a basic catalyst in methanol to a catalytic distillation column containing a heterogeneous basic catalyst defining a heterogeneous reaction zone, and feeding propylene oxide to the column. The methanol reacts with the propylene oxide according to a dual homogeneous catalytic reaction and heterogeneous catalytic reaction to form propylene glycol methyl ether, which is removed from the column as a bottoms product. Alternatively, methanol can be reacted with propylene oxide in a pre-reactor, to form propylene glycol methyl ether, and, when the temperature in the pre-reactor reaches about 100° C., the reaction products are transferred to the catalytic distillation column for further reaction.

21 Claims, 6 Drawing Sheets

PROCESS FOR PRODUCING PROPYLENE GLYCOL METHYL ETHER

FIELD OF INVENTION

This invention relates to a new process for producing propylene glycol methyl ether (PGME) from propylene oxide and methanol by catalytic distillation using a dual homogeneous/heterogeneous catalyst system.

PRIOR ART

Glycol ethers are a versatile class of organic solvent, having both alcohol and ether functionality. They are used as high-performance industrial solvents in paints, coatings, cleaners, resins, inks, in the manufacture of chemical intermediates, as anti-icing agents in jet fuels, fluids for hydraulic systems, and as chemical intermediate for plasticizers. The glycol ethers are clear, colorless liquids with mild, pleasant odors and low toxicity. They are water soluble and miscible with many organic solvents. They are prepared by the catalyzed reaction of alkylene oxides with different chain lengths of alcohols. In the case of propylene glycol ethers, they can be prepared using both acidic and basic catalysts. However, acidic catalysts are less selective and produce mixtures of isomeric product. Basic catalyzed reactions give products that are more selective to an α-isomer (also referred to as having a secondary alcohol structure) rather than β-isomers (primary alcohol structure).[1-3]

Basic catalysts can be classified as either homogeneous or heterogeneous. If the solid catalyst is soluble in the liquid reaction mixture so that a single liquid phase exists, it is said to be a homogeneous catalyst. If the solid catalyst is insoluble in the liquid reaction mixture it is said to be a heterogeneous catalyst.

Some current commercial processes employ homogeneous catalysts in the production of α-isomers of the propylene glycol ethers. The homogeneous basic catalysts such as alkali-metal hydroxides (employed by Shell Chemical) or amines (employed by Daicel Chemical) are used.

There are several recent patents that describe the production of glycol ethers using heterogeneous basic catalysts in liquid phase reactors: For example, in U.S. Pat. No. 6,291,720 Smith et al. describe a basic catalyst comprising a crystalline metallosilicate. Atkins et al., report in U.S. Pat. No. 5,110,992 on a catalyst based on the calcination of an anionic double hydroxide clay comprising magnesium and aluminum; they also report in U.S. Pat. No. 6,124,506 a catalyst comprising a layered double hydroxide clay having interlamellar anions which are inorganic metal anions, oxometallate or polyoxometallate anions. Further, U.S. Pat. No. 5,945,568 by Nagata et al. (1999) describes the use of a heterogeneous anion exchange resin which comprises a quaternary ammonium group with a linking group of chain length 3 or more. In U.S. Pat. No. 4,360,398, Sedon describes the use of a heterogeneous polymeric resin catalyst (eg. S-DVB, Nafion®, Dowex® MSC-1) with divalent metal counterions (e.g. iron or magnesium). In World patents WO2009/091379 and WO2009/091380 Li et al. describe a process for producing a propylene glycol monoalkyl ether using alkali or alkaline earth metal alkoxide catalysts and then using distillation for the separation of carbonyl impurities. In European Patent 0189247 Alderson and Green describe a process for the production of glycol ether using an anion exchange resin containing one or more amino groups. Some of the solid basic catalysts suffer from low activity and the difficulty with the anion exchange resins is low heat stability. As well, previous methods that employ liquid phase reactors still use distillation as a means to separate the product mixture. For reactors using anion exchange resins where heat stability of the catalyst is an issue, cooling of the reactor is required because the reaction of propylene oxide with methanol is a highly exothermic reaction.

Also, there is a review article on Reactive Distillation by G. Jan Harmsen in Chemical Engineering and Processing 46 (2007) 774-780, which discloses various homogeneous and heterogeneous catalysed reactions, including etherification, using individual basic catalysts, but not both.

Catalytic distillation (CD) which is known per se, provides the simultaneous processes of catalytic reaction and separation within a distillation column. Catalytic distillation can be further classified as either homogeneous or heterogeneous, depending on the type of catalyst used to carry out the reaction. A homogeneous catalyst can be introduced into the column with the feed. A heterogeneous catalyst is fixed within the distillation column. In the CD column both the reaction and distillation occur in the same space. Catalytic distillation offers many advantages to conventional two-step process of reaction followed by separation. Some of the advantages include: reduced operating (e.g. energy) and maintenance costs, lower capital costs, higher conversion and selectivity, improved separation in cases where azeotropic mixtures are formed in the reactor. Catalytic distillation is particularly suitable for equilibrium-limited reactions as the simultaneous separation of products from the reactants in the column provides the driving force for reaction to proceed in the forward direction. Catalytic distillation is also advantageous for exothermic reactions where the heat of reaction contributes to the heat input to the reboiler of the distillation column. Also, there is no need to remove heat, as is the case with a conventional reactor, so the cooling water requirement will be less. Depending on operating conditions and kinetics, catalytic distillation can also be used advantageously to suppress or minimize the amount of byproducts produced, or to achieve azeotropic separation by reacting one of the components away.

SUMMARY OF THE INVENTION

According to one embodiment of the invention, a process is provided for producing propylene glycol methyl ether comprising
 (a) dissolving a solid basic catalyst in methanol to form a homogeneous solution,
 (b) feeding the solution to a catalytic distillation column containing a heterogeneous basic catalyst fixed in place in the column and defining a heterogeneous reaction zone,
 (c) feeding propylene oxide to the column,
wherein, in the column, methanol reacts with propylene oxide according to a dual homogeneous catalytic reaction and heterogeneous catalytic reaction to form propylene glycol methyl ether, and
 (d) removing substantially pure propylene glycol methyl ether from the column as a bottoms product.

The catalytic distillation column preferably includes a plurality of numbered stages, arranged numerically from top to bottom, and wherein the homogeneous catalyst/methanol solution is fed to the column near the top and the propylene oxide is fed to the column near the bottom.

The preferred heterogeneous basic catalyst is an anion exchange resin (free base form), e.g. weak anionic resins based on a highly macroporous, cross-linked, styrene divinyl benzene polymer structure, having a tertiary amine functionality of the formula (R—N—(CH$_3$)$_2$). Such resins are sold under the trademarks Amberlyst® 21, dried, from Dow Chemical Company, and Diaion® WA30, from Mitsubishi Chemical Company.

A suitable homogeneous basic catalyst is anhydrous sodium methoxide (97% anhydrous form) or potassium methoxide.

Preferably, the pressure in the catalytic distillation column is about 1.8 to 4 atm, preferably about 3 atm.

The temperature in the heterogeneous reaction zone in the distillation column is maintained at about 70 to 100° C. The temperatures above and below the heterogeneous reaction zone are in the range of 50 to 70° C. and 100 to 160° C., respectively.

The molar feed ratio of methanol to propylene oxide to the catalytic distillation column is between 1.5 and 5, preferably about 3.44.

The amount of heterogeneous catalyst in the distillation column is 150 to 500 kg per 1000 kg/h of propylene oxide feed.

The amount of homogeneous catalyst in the methanol feed is in the range of 0.001 to 0.01 of the weight of the heterogeneous catalyst used.

The catalytic distillation column includes 10-20 stages, preferably 20 stages.

The catalytic distillation column includes stages numbered 1 to 20, wherein the heterogeneous catalyst is located at stages 4 to 7, the homogeneous catalyst in methanol solution is fed to the column at stage 2, and the propylene oxide is fed to the column at stage 9.

In another embodiment of this process, the process involves a liquid phase pre-reactor containing a basic heterogeneous catalyst fixed in place therein, the pre-reactor being in fluid communication with the catalytic distillation column. The homogeneous catalyst in methanol solution and propylene oxide are first fed to the pre-reactor where methanol reacts with propylene oxide according to a dual homogeneous catalytic reaction and heterogeneous catalytic reaction to form propylene glycol methyl ether and when the temperature in the pre-reactor reaches about 100° C., transferring the reaction products to a catalytic distillation column containing a heterogeneous basic catalyst fixed in place therein and defining a heterogeneous reaction zone for further reaction.

According to another embodiment of the invention the process comprises the steps of
 (a) dissolving a solid basic catalyst in methanol to form a homogeneous solution,
 (b) feeding the solution to a liquid phase pre-reactor containing a heterogeneous basic catalyst fixed in place therein, operating adiabatically,
 (c) feeding propylene oxide to the pre-reactor, wherein methanol reacts with propylene oxide according to a dual homogeneous catalytic reaction and heterogeneous catalytic reaction to form propylene glycol methyl ether,
 (d) when the temperature in the pre-reactor reaches about 100° C., transferring the reaction products so formed to a catalytic distillation column containing a heterogeneous basic catalyst fixed in place therein defining a heterogeneous reaction zone, and where additional methanol may be added to a catalytic distillation column for further reaction, and where additional methanol may be added to the catalytic distillation column for further reaction, and
 (e) removing substantially pure propylene glycol methyl ether from the distillation column as a bottoms product.

The catalytic distillation (CD) column preferably includes ten stages numbered 1 to 10, and the heterogeneous catalyst is located at stages 2 to 6, the homogeneous reaction occurs at stage 6, ie., where the reaction products from the pre-reactor are fed into the CD column, the pressure in the CD column is about 2.5 atm and the pressure in the pre-reactor is about 0.2 to 0.5 atm higher than that in the CD column.

The addition of an alkaline solution in the form of the basic homogeneous catalyst, e.g. anhydrous sodium methoxide, dissolved in methanol in the feed mixture prevents the deactivation of the heterogeneous catalyst resin. The alkaline solution also shows catalytic activity towards the reaction to form PGME. In this dual catalyst homogeneous (dissolved sodium methoxide) and heterogeneous (insoluble solid anion exchange resin) system, we are able to continuously regenerate the resin catalyst and simultaneously obtain the enhanced activity from the presence of sodium methoxide.

DETAILED DESCRIPTION OF THE INVENTION

Catalyst Comparison

Figure 1:
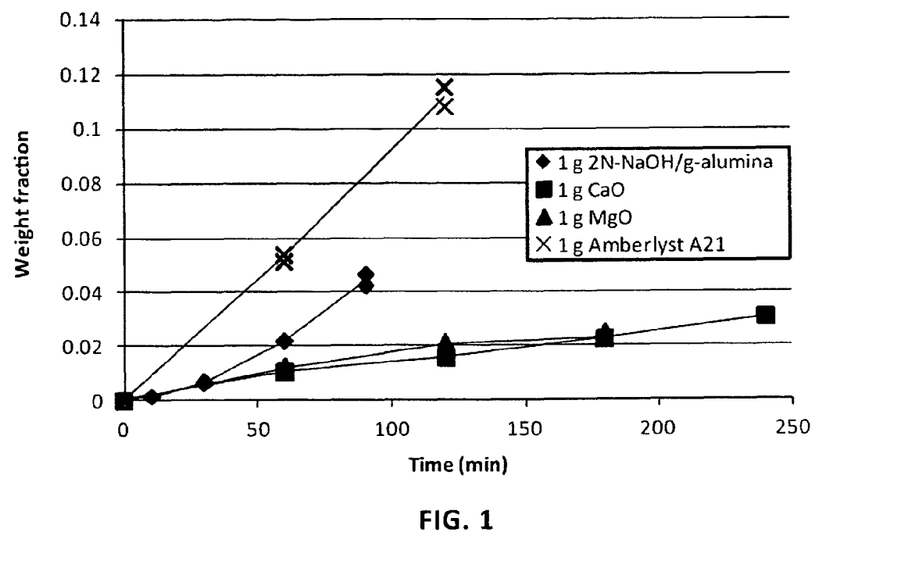
FIG. 1 is a graph illustrating the activity of various basic catalysts for the production of PGME from the reaction of propylene oxide and methanol.

Several basic catalysts were examined for their activity for the production of PGME. Catalytic activity experiments were performed using homogeneous, heterogeneous, and dual homogeneous/heterogeneous basic catalysts. Batch experiments were performed in an autoclave reactor at a temperature of 90° C. and pressure of 88 psig using 1 g catalyst and 55 g feed. The feed weight ratio was 2:1 methanol to propylene oxide. The results are shown in FIG. 1.

Heterogeneous Catalysts

The heterogeneous basic catalysts CaO (Fisher, certified ACS) and MgO (Alfa Aesar, 96% min., 325 mesh) were used in powder form (as received). The NaOH/γ-alumina was prepared from crushed γ-alumina (<20 mesh): 50 mL of 2N NaOH was added to 15 g of the γ-alumina and allowed to stand overnight. The solution was heated in a drying oven at 200° C. for 14 hours, and then cooled to room temperature. The resulting cake was crushed and washed with small amounts of methanol until the methanol was neutral, as tested with litmus paper. The heterogeneous anion exchange resins (free base form) were supplied by Dow Chemical Company (Amberlyst® 21, dried) and Mitsubishi Chemical Company (Diaion® WA30 and WA20, wet form).

Homogeneous Catalysts

The homogeneous basic catalyst tested were sodium methoxide, $CH_3ONa$ (97%, anhydrous form) and potassium methoxide, $CH_3OK$, supplied by Acros and Aldrich chemicals. Sodium hydroxide (NaOH) and potassium hydroxide (KOH) are not suitable because when dissolved in solution they contribute to the formation of glycols, which are considered undesirable byproducts to our process.

From FIG. 1 it can be seen that the heterogeneous catalysts, anion exchange resins show the highest activity. With some of the catalysts there were also traces of byproducts (dipropylene glycol methyl ether, DPGME) produced, but, since they were not in significant amounts, the DPGMEs were not included in the kinetic models developed for process design using Aspen Plus® simulation program.

Figure 2:
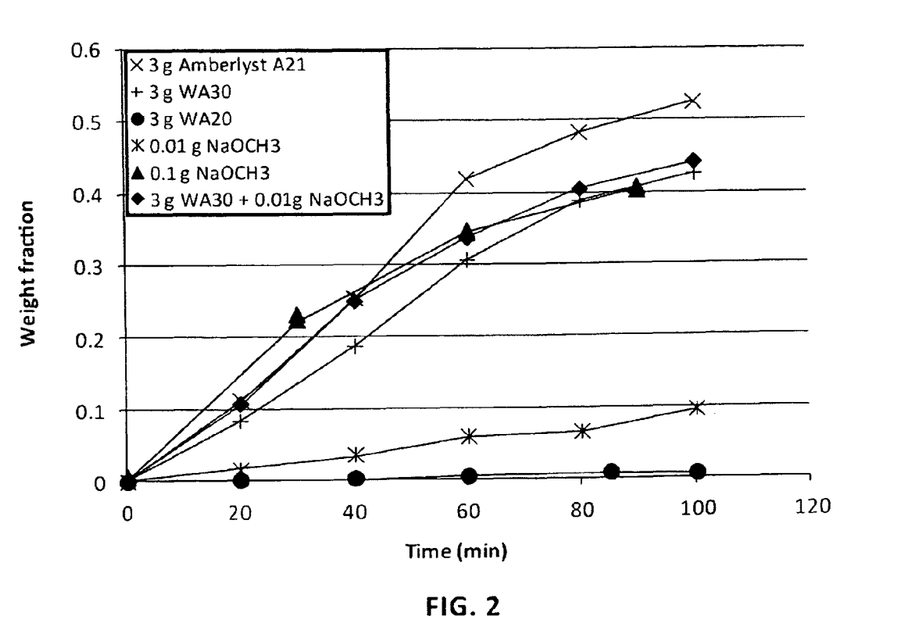
FIG. 2 is a graph illustrating the activity of various catalysts for the production of PGME at the following reaction conditions: T=90° C., P=88 psig, Feed=75 g, weight ratio MeOH/PO=2:1.

FIG. 2 compares the activity of homogeneous and heterogeneous basic catalysts and dual homogeneous/heterogeneous basic catalysts. While A21 and WA30 show similar activity, WA20 has very low activity. It is noted that WA20 is a 'strongly' basic anionic resin and falls into a different class of anionic exchange resins than WA30 (ie. different functionality). Aside from its poor performance as a catalyst, it also has much lower temperature stability. As well, the homogeneous catalyst sodium methoxide also shows activity for the production of PGME. The presence of a small amount of homogeneous catalyst in combination with the anion exchange catalysts increases the overall activity though not on a purely additive basis. Other tests also show that on a molar basis the homogeneous catalysts, sodium methoxide and potassium methoxide, have similar activities.

Characteristics of Anion Exchange Resins

The heterogeneous basic anion exchange catalysts used in this work (A21 and WA30) are weak basic resins based on a highly macroporous, crosslinked, styrene divinyl benzene (S-DVB) polymer structure with tertiary amine functionality ($R-N(CH_3)_2$). These resins are described as having a broad pore size distribution, excellent mechanical and osmotic strength, chemical stability, and a thermal stability up to 100° C. A typical structural representation of the tertiary amine S-DVB anion exchange resin is given as follows.

Loss of catalytic activity from ion exchange resins can be attributed to neutralization of the functional groups, dissolution of the functional groups into the reaction mixture, and fouling/blockage of the active sites by products/byproducts. The weakly basic anion exchange resins can be regenerated using alkaline solutions. It is noted that according to the invention, deactivation of heterogeneous resin catalyst is prevented by the presence of the homogeneous catalyst dissolved in methanol in the feed to form an alkaline solution.

Case 1: Conventional Liquid Phase Reactor (Prior Art)

Figure 3:
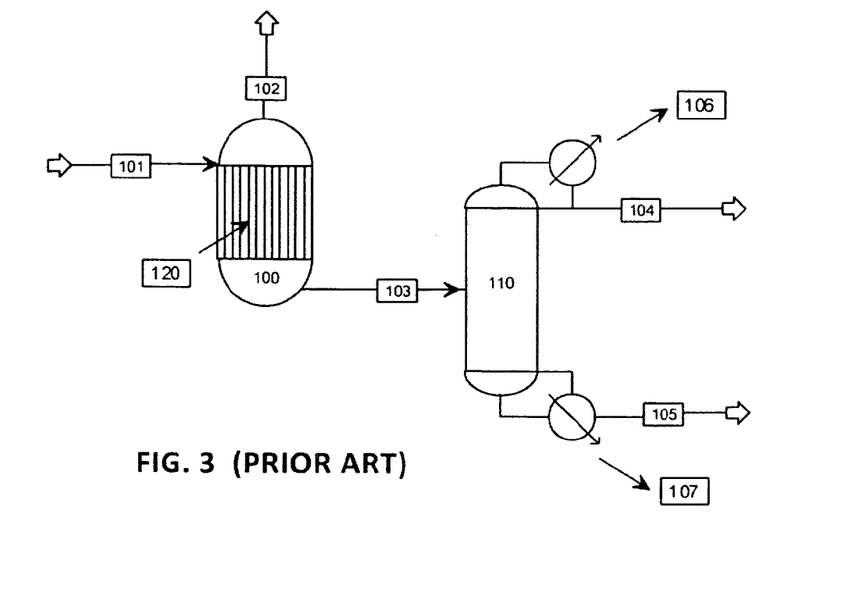
FIG. 3 (PRIOR ART) is a schematic illustration of an apparatus for performing the traditional multi-column process for the production of PGME.

As seen in FIG. 3, the traditional process consists of a reactor 100 followed by a distillation column 110. The reactor (EQMREACT) is modeled as an equilibrium reactor operating at 100° C. and a pressure of 3 atm. This is to ensure that a total liquid phase is present in the reactor. A cooling coil 120 is used to maintain the reactor at the desired temperature setpoint. All simulations for the following cases are based on a feed rate of 1900 kg/h methanol and 1000 kg/h propylene oxide. Any basic catalyst may be used in the reactor as long as sufficient reaction time is allowed in order for the reaction to proceed to equilibrium conversion. It is noted that in the simulation we just calculated the cooling water requirement not the reactor size.

The feed to the reactor (stream 101) has a molar feed ratio of methanol to propylene oxide of 3.44. Stream 101 enters the reactor at 25° C. The reaction occurs in reactor 100 and the liquid products exit the reactor as stream 103 which are then fed to distillation column D for separation. Since the reaction is carried out in the liquid phase the content of the distillate stream (102) is zero. Unreacted methanol is recovered in distillate stream 104 and the PGME product is taken from bottoms stream 105. A condenser 106 and a reboiler 107 are provided for cooling and heating, respectively. The operating parameters of the distillation column are given in Table 1.

TABLE 1

| Operating parameters of the distillation column | |
|---|---|
| Parameter | Value |
| Column pressure (atm) | 1 |
| Distillate to feed ratio (D/F) | 0.709 |
| Reflux ratio (RR) | 2 |
| Total number of stages | 10 |
| Feed stage | 5 |

Figure 4:
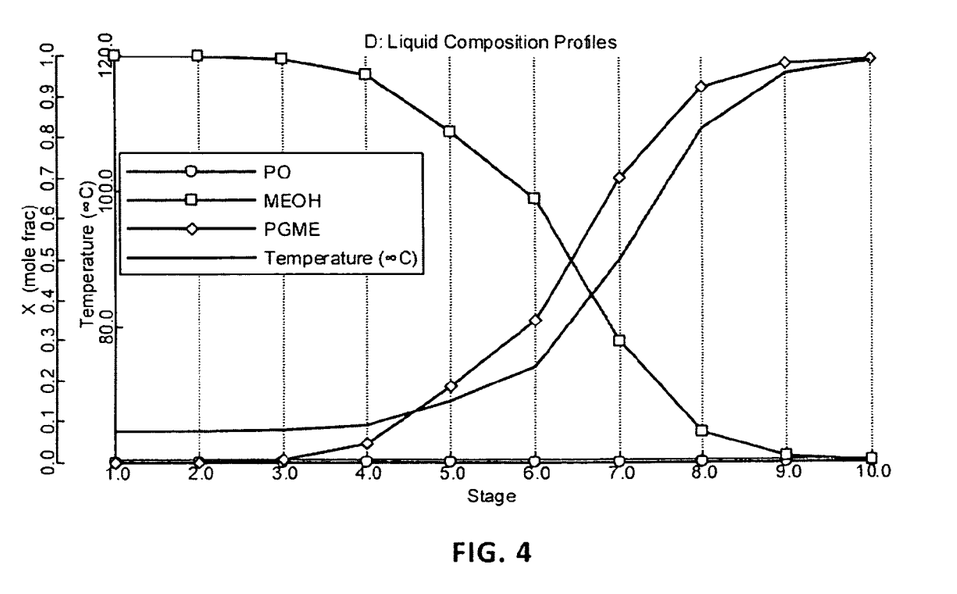
FIG. 4 is a graph illustrating liquid composition and temperature profiles along the length of the distillation column.

FIG. 4 shows composition and temperature profiles for the distillation column in an optimized conventional process for the production of PGME. Table 2 shows the stream compositions for the distillation column. Table 3 shows stage profiles for the distillation column. The cooling duty of the reactor (EQMREACT) is −784836 kJ/h. It can be seen from Table 3 that the cooling duty for the condenser 106 (Stage 1) and heating duty for the reboiler 107 (Stage 10) of the distillation column (D) are −4433808 kJ and 4327372 kJ, respectively.

TABLE 2

| Stream compositions for the distillation column. | | | |
|---|---|---|---|
| Substream: MIXED | 103 | 104 | 105 |
| Mole Flow kmol/hr | | | |
| PO | 1.03E−07 | 1.03E−07 | 3.09E−13 |
| MEOH | 42.07926 | 42.03363 | 0.045623 |
| PGME | 17.21762 | 0.007851 | 17.20977 |
| Mole Frac | | | |
| PO | 1.74E−09 | 2.46E−09 | 1.79E−14 |
| MEOH | 0.709637 | 0.999813 | 0.002644 |
| PGME | 0.290363 | 0.000187 | 0.997356 |
| Mass Flow kg/hr | | | |
| PO | 6E−06 | 6E−06 | 1.8E−11 |
| MEOH | 1348.31 | 1346.848 | 1.461874 |
| PGME | 1551.69 | 0.707576 | 1550.982 |

TABLE 2-continued

Stream compositions for the distillation column.

| Substream: MIXED | 103 | 104 | 105 |
|---|---|---|---|
| Mass Frac | | | |
| PO | 2.07E−09 | 4.45E−09 | 1.16E−14 |
| MEOH | 0.464935 | 0.999475 | 0.000942 |
| PGME | 0.535065 | 0.000525 | 0.999058 |
| Liq Vol 60F l/min | | | |
| PO | 1.22E−07 | 1.22E−07 | 3.64E−13 |
| MEOH | 28.2875 | 28.25683 | 0.03067 |
| PGME | 28.19385 | 0.012856 | 28.18099 |
| LiqVolFrac60F | | | |
| PO | 2.15E−09 | 4.3E−09 | 1.29E−14 |
| MEOH | 0.500829 | 0.999545 | 0.001087 |
| PGME | 0.499171 | 0.000455 | 0.998913 |
| Total Flow kmol/hr | 59.29688 | 42.04149 | 17.25539 |
| Total Flow kg/hr | 2900 | 1347.556 | 1552.444 |
| Total Flow l/min | 63.57637 | 30.18435 | 34.54049 |
| Temperature ° C. | 100 | 64.53892 | 119.6505 |
| Pressure atm | 3 | 1 | 1 |

TABLE 3

Stage profile for the distillation column

| Stage | Temperature C | Pressure Atm | Heat duty kJ/hr | Liquid flow kg/hr | Vapor flow kg/hr | Liquid feed kg/hr | Vapor feed kg/hr |
|---|---|---|---|---|---|---|---|
| 1 | 64.5389201 | 1 | −4433808 | 2695.112 | 0 | 0 | 0 |
| 2 | 64.5683964 | 1 | 0 | 2700.238 | 4042.668 | 0 | 0 |
| 3 | 64.7264493 | 1 | 0 | 2727.591 | 4047.794 | 0 | 0 |
| 4 | 65.5510121 | 1 | 0 | 2866.587 | 4075.147 | 0 | 235.0405 |
| 5 | 69.1016095 | 1 | 0 | 5730.272 | 3979.103 | 2664.959 | 0 |
| 6 | 74.0705872 | 1 | 0 | 6723.726 | 4177.833 | 0 | 0 |
| 7 | 90.1237226 | 1 | 0 | 8849.018 | 5171.281 | 0 | 0 |
| 8 | 109.41764 | 1 | 0 | 10627.43 | 7296.572 | 0 | 0 |
| 9 | 117.712601 | 1 | 0 | 11351.52 | 9074.981 | 0 | 0 |
| 10 | 119.650535 | 1 | 4327372 | 1552.444 | 9799.077 | 0 | 0 |

Case 2: Catalytic Distillation Column According to the Invention

Figure 5:
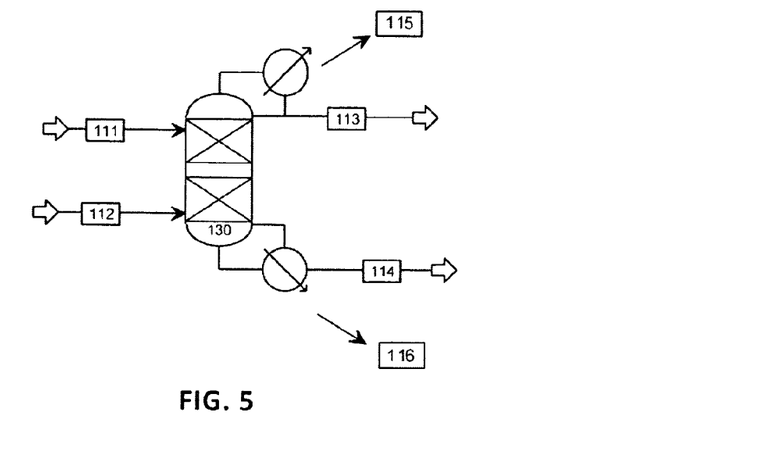
FIG. 5 is a schematic illustration of a catalytic distillation apparatus according to the invention for PGME synthesis.

The catalytic distillation column 130 shown in FIG. 5 is modeled with two reactions (homogenous and heterogeneous). The kinetic rate expressions were developed by correlating laboratory rate data from batch experiments in the temperature range of interest, and using these rate expressions for Aspen Plus® simulations. The heterogeneous basic anion exchange resin catalyst and reaction occurs in the column only on the stages on which it is placed. The homogeneous catalyst $CH_3ONa$, is dissolved in methanol and reaction in the column occurs on any stages on or below where the feed enters the column. Since the homogeneous catalyst is not volatile, it cannot vaporize and condense on the stages above the feed point. The homogeneous catalyst/methanol solution is fed near the top of the column via stream 111, while propylene oxide, the more volatile component, enters near the bottom in stream 112. Unreacted methanol is recovered in stream 113 and product PGME is taken from stream 114. Condenser 115 and reboiler 116 are included to provide cooling and heating, respectively.

Two examples are presented for Case 2: 2.1 heterogeneous catalyst alone and 2.2 homogeneous and heterogeneous catalysts together.

Table 4 shows the operating parameters of the catalytic distillation column for the base case. These parameters have been optimized to provide greater than 99% conversion of PO, a minimum PGME purity of 99% in the bottoms product, and to ensure a working temperature of ≤100° C. in the heterogeneous reaction zone of the CD column.

TABLE 4

Parameter values for base case CD column used in Aspen Plus ® simulations

| | Value | |
|---|---|---|
| Parameter | Example 2.1 | Example 2.2 |
| Column pressure (atm) | 3 | 3 |
| Distillate to feed ratio (D/F) | 0.55 | 0.55 |
| Reflux ratio (RR) | 1.5 | 1.5 |
| Total number of stages | 20 | 20 |
| Reaction stage location | Stages 4-9 | Stages 2-20 |
| Homogeneous | 4-9 | 2-3 |
| Homogeneous + heterogeneous | | 4-9 |
| Homogeneous | | 10-20 |

TABLE 4-continued

Parameter values for base case CD column used in Aspen Plus ® simulations

| | Value | |
|---|---|---|
| Parameter | Example 2.1 | Example 2.2 |
| Feed stage location (above stage) | | |
| Methanol | 2 | 2 |
| Propylene oxide | 9 | 9 |
| Molar feed ratio of methanoL:propylene oxide | 3.44 | 3.44 |

Example 2.1

Heterogeneous Catalyst (Base Case)

In this example the heterogeneous catalyst (anion exchange resin) is packed on stages 4 to 9 of the CD column.

Example 2.2

Heterogeneous and Homogeneous Catalyst

In this example both heterogeneous and homogeneous catalysts are used, and the reaction parameters are shown in Table 4. The heterogeneous catalyst is packed on stages 4 to 9 of the CD column and the homogeneous catalyst, which is dissolved in the methanol feed stream 111, enters the CD column on stage 2. Homogeneous reaction occurs on stages 2 to 20, whereas the heterogeneous reaction takes place only on stages 4 to 9. Propylene oxide is fed to the column at stage 9.

Figure 6:
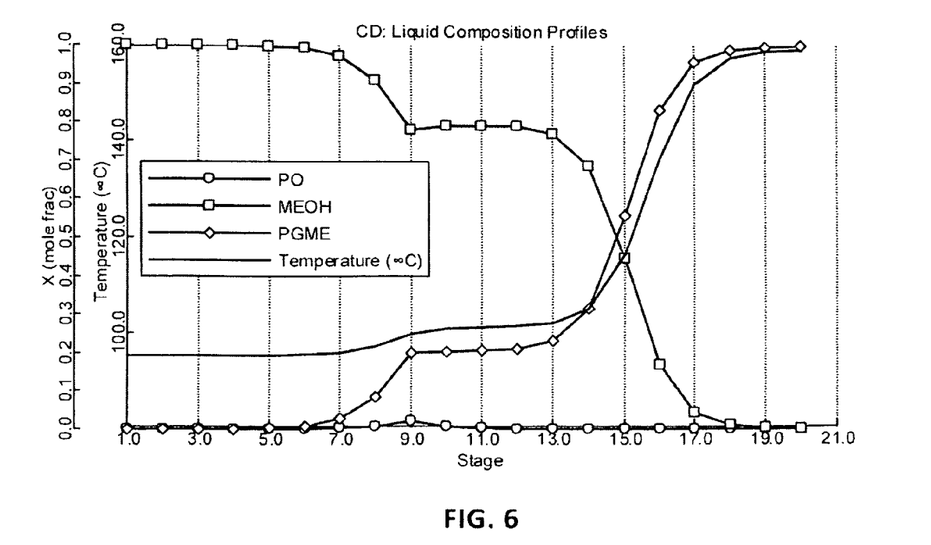
FIG. 6 is a graph illustrating liquid composition and temperature profiles in a catalytic distillation column of FIG. 5.

The following results are presented for Example 2.2. FIG. 6 shows composition and temperature profiles for the CD column. Table 5 shows the stream compositions for the CD column and Table 6 shows stage profiles for the CD column. From Table 6, the cooling duty for the condenser (Stage 1) and heating duty for the reboiler (Stage 20) of the CD column are −3464913 kJ and 2878928 kJ, respectively. Cooling Duties for Examples 2.1 and 2.2 are presented in Table 10.

TABLE 5

Stream composition for CD column.

| Substream: MIXED | 111 | 112 | 113 | 114 |
|---|---|---|---|---|
| Mole Flow kmol/hr | | | | |
| PO | 0 | 17.21762 | 0.0054877 | 7.6034E−08 |
| MEOH | 59.29688 | 0 | 42.077261 | 0.00748455 |
| PGME | 0 | 0 | 0.0002241 | 17.2119071 |
| Mole Frac | | | | |
| PO | 0 | 1 | 0.0001304 | 4.4156E−09 |
| MEOH | 1 | 0 | 0.9998643 | 0.00043465 |
| PGME | 0 | 0 | 5.325E−06 | 0.99956534 |
| Mass Flow kg/hr | | | | |
| PO | 0 | 1000 | 0.3187275 | 4.4161E−06 |
| MEOH | 1900 | 0 | 1348.2463 | 0.23982127 |
| PGME | 0 | 0 | 0.0201963 | 1551.17493 |
| Mass Frac | | | | |
| PO | 0 | 1 | 0.0002363 | 2.8465E−09 |
| MEOH | 1 | 0 | 0.9997487 | 0.00015458 |
| PGME | 0 | 0 | 1.498E−05 | 0.99984542 |
| Liq Vol 60F l/min | | | | |
| PO | 0 | 20.2445 | 0.0064525 | 8.9401E−08 |
| MEOH | 39.86193 | 0 | 28.286158 | 0.00503144 |
| PGME | 0 | 0 | 0.000367 | 28.1844975 |
| LiqVolFrac60F | | | | |
| PO | 0 | 1 | 0.0002281 | 3.1714E−09 |
| MEOH | 1 | 0 | 0.999759 | 0.00017848 |
| PGME | 0 | 0 | 1.297E−05 | 0.99982151 |
| Total Flow kmol/hr | 59.29688 | 17.21762 | 42.082972 | 17.2193917 |
| Total Flow kg/hr | 1900 | 1000 | 1348.5852 | 1551.41476 |
| Total Flow l/min | 39.93673 | 20.27052 | 31.987828 | 36.755131 |
| Temperature C. | 25 | 25 | 95.34927 | 159.160221 |
| Pressure atm | 3 | 3 | 3 | 3 |

TABLE 6

Stage profile for the CD column.

| Stage | Temperature C | Pressure Atm | Heat duty kJ/hr | Liquid flow kg/hr | Vapor flow kg/hr | Liquid feed kg/hr |
|---|---|---|---|---|---|---|
| 1 | 95.34927 | 3 | −3464913 | 2022.878 | 0 | 0 |
| 2 | 95.35563 | 3 | 0 | 4383.184 | 3371.463 | 1900 |
| 3 | 95.35804 | 3 | 0 | 4383.423 | 3831.769 | 0 |
| 4 | 95.3707 | 3 | 0 | 4383.023 | 3832.009 | 0 |
| 5 | 95.40828 | 3 | 0 | 4382.265 | 3831.608 | 0 |
| 6 | 95.53839 | 3 | 0 | 4379.336 | 3830.85 | 0 |
| 7 | 95.9767 | 3 | 0 | 4365.199 | 3827.921 | 0 |
| 8 | 97.2914 | 3 | 0 | 4276.624 | 3813.784 | 0 |
| 9 | 99.73144 | 3 | 0 | 4390.29 | 3725.209 | 1000 |
| 10 | 100.9104 | 3 | 0 | 4338.435 | 2838.875 | 0 |
| 11 | 101.3087 | 3 | 0 | 4325.495 | 2787.02 | 0 |
| 12 | 101.5521 | 3 | 0 | 4337.358 | 2774.081 | 0 |
| 13 | 102.2368 | 3 | 0 | 4420.147 | 2785.943 | 0 |
| 14 | 105.3127 | 3 | 0 | 4789.882 | 2868.733 | 0 |
| 15 | 116.2496 | 3 | 0 | 5828.061 | 3238.467 | 0 |
| 16 | 136.4811 | 3 | 0 | 7245.832 | 4276.646 | 0 |
| 17 | 151.8964 | 3 | 0 | 8272.367 | 5694.417 | 0 |
| 18 | 157.4658 | 3 | 0 | 8671.433 | 6720.952 | 0 |
| 19 | 158.8523 | 3 | 0 | 8774.543 | 7120.018 | 0 |
| 20 | 159.1602 | 3 | 2878928 | 1551.415 | 7223.128 | 0 |

The effect of various process parameters was investigated and their range is described herein:

Since some of the variables are dependent on one another, it is required that some process parameters change concomitantly to ensure optimum operation of the CD column. The preferred molar feed ratio of methanol to propylene oxide is from 1.5 to 5, which corresponds to a preferred distillate to feed ratio of 0.2 to 0.67. More preferably, the molar feed ratio is about 3.44, which corresponds to a distillate to feed ratio of 0.55.

The preferred temperature range of the heterogeneous reaction zone is 70 to 100° C.

The preferred location of the heterogeneous reaction zone is between the feed streams 111 and 112 ie. between stages 2 and 9.

The propylene oxide feed stream 112 may be located as a single feed stream at the bottom of the heterogeneous catalyst zone near stage 9, or as multiple feed streams on any of the stages 4-9 within the heterogeneous reaction zone of the CD column.

The preferred operating pressure of the CD column is between 1.8 and 4 atm. More preferably, the operating pressure is about 3 atm.

Example 2.3

Molar Feed Ratio=1.5

Figure 7:
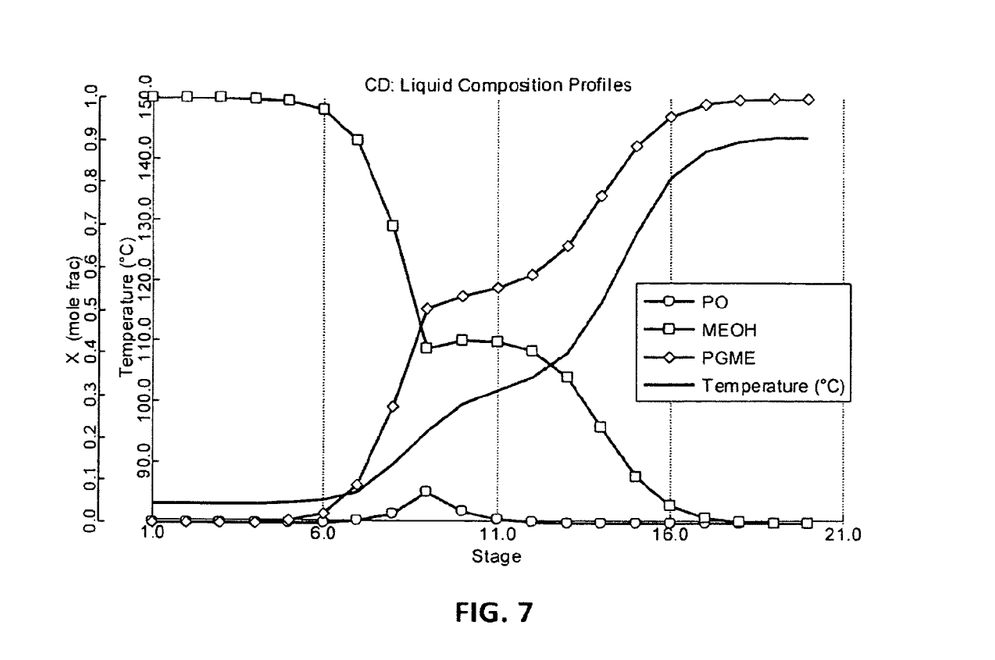
FIG. 7 is a graph illustrating liquid composition and temperature profiles along the length of the distillation column (Example 2.3)

The CD column is run with a molar feed ratio=1.5, D/F=0.2, P=2 atm, RR=5, and all other conditions are as in Example 2.2 (Table 4). The heterogeneous reaction zone temperature is maintained in the range of 83 to 95° C. See FIG. 7.

Example 2.4

Molar Feed Ratio=5

Figure 8:
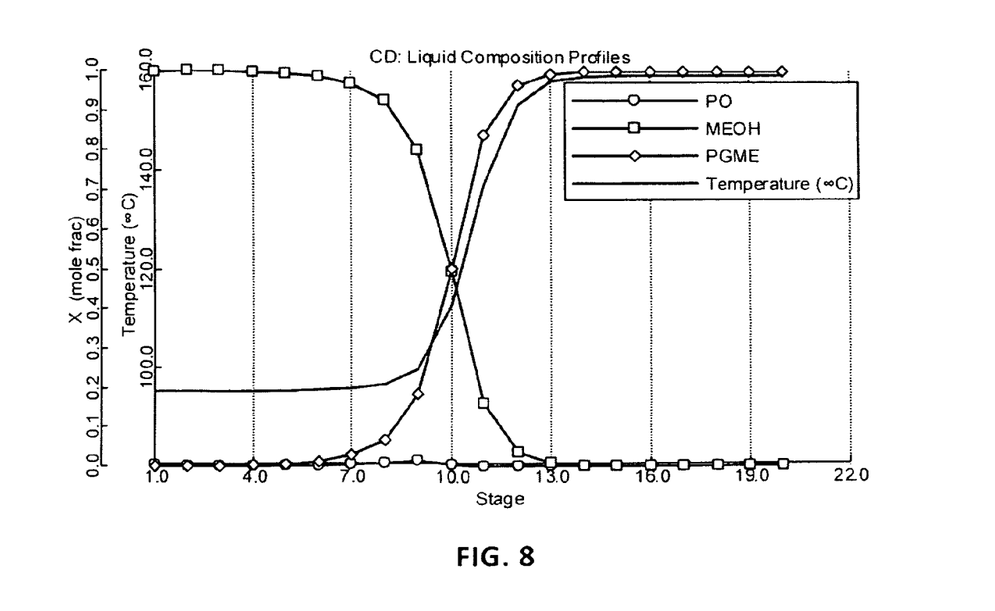
FIG. 8 is a graph illustrating liquid composition and temperature profiles along the length of the distillation column (Example 2.4)

The CD column is run with a molar feed ratio=5, D/F=0.67, P=3 atm, RR=3.2, and all other conditions are as in Example 2.2 (Table 4). The reaction zone temperature is maintained in the range of 95 to 100° C. See FIG. 8.

Example 2.5

Total Reflux

Figure 9:
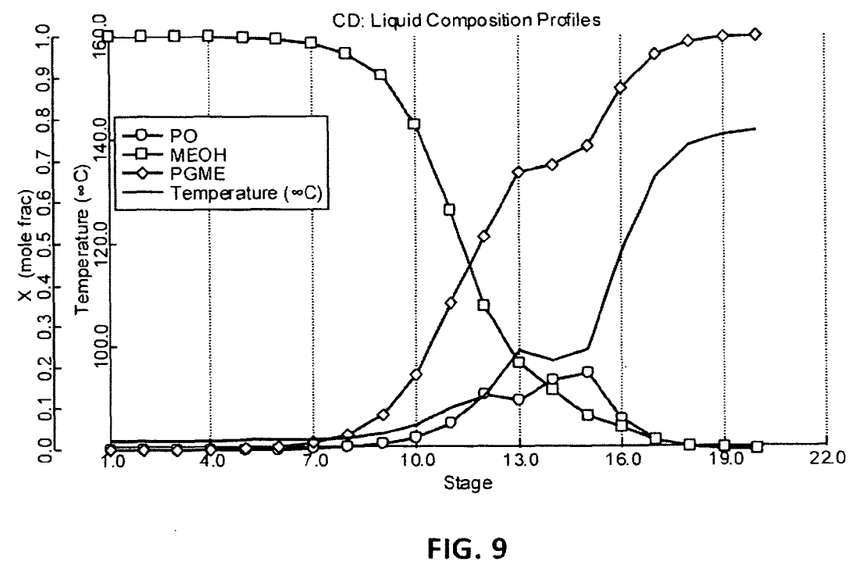
FIG. 9 is a graph illustrating liquid composition and temperature profiles along the length of the distillation column (Example 2.5)

In this example the CD column operates with a reboiler, and a condenser at total reflux. The propylene oxide feed is split evenly between stage 12 and 15, the heterogeneous reaction zone is located between stages 2-13 and on stage 15. All other conditions are as in Example 2.1 (Table 4), except the methanol feed is introduced onto stage 1. The heterogeneous reaction zone temperature is between 82 to 100° C. See FIG. 9.

From example 2.5, by splitting the propylene oxide feed over multiple stages, the temperature in the reaction zone is more evenly distributed and easier to keep the operation below 100° C.

Examples 2.3 to 2.5 shows that by varying the molar feed ratio the other operating variables must be adjusted to obtain optimum design.

Case 3: Catalytic Distillation Column with Pre-Reactor

Figure 10:
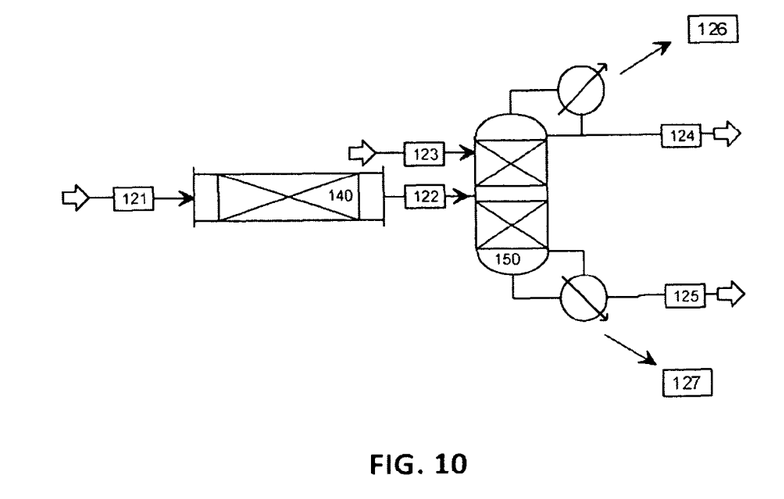
FIG. 10 is a schematic illustration of a catalytic distillation apparatus including a pre-reactor according to the invention for PGME synthesis.

In Case 1 (prior art) it was shown that energy is lost when an isothermal reactor is required to operate ≤100° C. The reactor is limited to 100° C. so as to prevent thermal degradation of the catalyst, and therefore, cooling of the reactor is required. This is energy lost from the process. In Case 3 we model a CD column with a pre-reactor 140 (FIG. 10). The pre-reactor is modeled as a plug flow reactor (PFR) with a mixed methanol and propylene oxide feed stream 121 to the liquid phase reactor PFR. The reactor PFR is allowed to operate adiabatically (without cooling) up until 100° C. at which point the exit stream 122 is fed to the catalytic distillation column 150 to allow for additional reaction and separation of the products to occur. Additional methanol may be fed to the catalytic distillation column through stream 123. Unreacted methanol is recovered in distillate stream 124 and product PGME is taken from bottoms stream 125. The benefit of this configuration is to take advantage of the increased rate of reaction which occurs when feed concentrations are at their highest. However, this scheme would require extra contact time at lower reaction temperature in the first part of the PFR.

Two examples are presented for Case 3: heterogeneous catalyst only (case 3.1), in both the PFR 140 and in CD column 150, and both heterogeneous and homogeneous catalyst in both PFR 140 and CD column 150 (case 3.2). The plug flow liquid phase reactor and CD column operating parameters are shown in Table 7.

Example 3.1

Heterogeneous Catalyst

In this example heterogeneous catalyst is packed in the PFR 140 and on stages 2 to 6 of the CD column 150, containing 10 stages.

Example 3.2

Heterogeneous and Homogeneous Catalyst

In this example heterogeneous catalyst is packed in the PFR 140 and on stages 2 to 6 of CD column 150 containing 10 stages. Homogeneous catalyst enters the PFR dissolved in the mixed methanol and propylene oxide feed stream 121, such that both homogeneous and heterogeneous catalytic reactions occur in both PFR 140 and CD column 150. The homogeneous reaction occurs on stage 6 of CD column 150 as this is where stream 122 enters the column.

Figure 11:
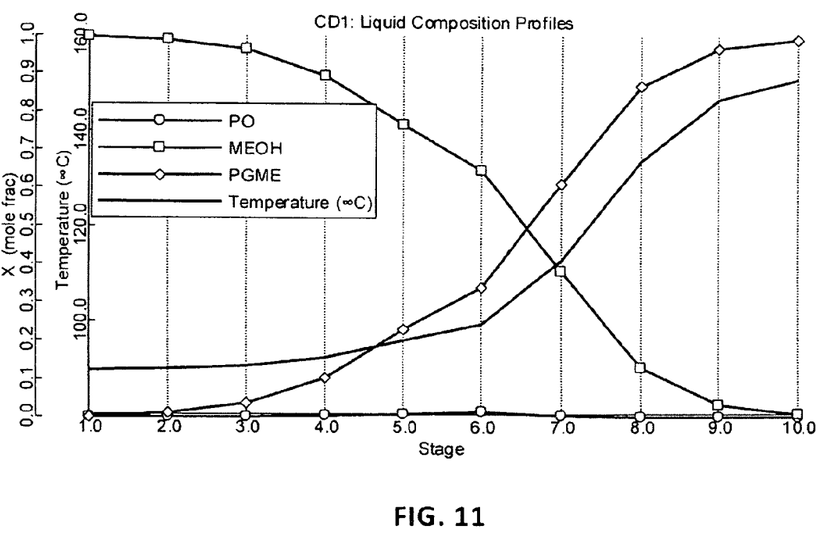
FIG. 11 is a graph illustrating composition and temperature profiles along the length of the catalytic distillation column of FIG. 10.

FIG. 11 shows the composition and temperature profiles along the length of the CD column 150. A slightly lower column pressure of 2.5 Atm in the CD column 150 ensures that the reaction zone temperature is ≤100° C. Table 8 shows the stream compositions for CD column 150 and Table 9 shows stage profiles for CD column 150. It can be seen from Table 9 that the cooling duty for the condenser 126 (Stage 1) and heating duty for the reboiler 127 (Stage 10) of the catalytic distillation column 150 are −3511269 Id and 2918085 kJ, respectively. Cooling Duties for Examples 3.1 and 3.2 are presented in Table 10.

TABLE 7

Operating parameters for the PFR and CD column.

| | Value | |
|---|---|---|
| Parameter | Example 3.1 | Example 3.2 |
| PFR | | |
| Length (m) | 15 | 15 |
| Diameter (m) | 0.5 | 0.5 |
| $T_{inlet}$ (° C.) | 20 | 20 |
| $T_{outlet}$ (° C.) | 66.7 | 88 |
| Residence time (min) | 24 | 24 |
| Molar feed ratio of methanol:propylene oxide | 3.44 | 3.44 |
| CD column: | | |
| Column pressure (atm) | 2.5 | 2.5 |
| Distillate to feed ratio (D/F) | .588 | 0.608 |
| Reflux ratio (RR) | 1.5 | 1.5 |
| Total number of stages | 10 | 10 |

TABLE 7-continued

Operating parameters for the PFR and CD column.

| | Value | |
|---|---|---|
| Parameter | Example 3.1 | Example 3.2 |
| Reaction stage location | 2-6 | 2-6 |
| Heterogeneous | 2-6 | 2-5 |
| Homogeneous + heterogeneous | | 6 |
| Feed stage location (above stage) | 6 | 6 |

TABLE 8

Stream composition for CD1 column.

| Substream: MIXED | 122 | 123 | 124 |
|---|---|---|---|
| Mole Flow kmol/hr | | | |
| PO | 9.920056 | 0.027808 | 0.000452 |
| MEOH | 51.99931 | 41.99387 | 0.113649 |
| PGME | 7.297563 | 0.062219 | 17.12714 |
| Mole Frac | | | |
| PO | 0.143318 | 0.000661 | 2.62E−05 |
| MEOH | 0.751251 | 0.997861 | 0.006592 |
| PGME | 0.10543 | 0.001478 | 0.993382 |
| Mass Flow kg/hr | | | |
| PO | 576.1572 | 1.615071 | 0.026261 |
| MEOH | 1666.17 | 1345.574 | 3.641566 |
| PGME | 657.6724 | 5.607325 | 1543.536 |
| Mass Frac | | | |
| PO | 0.198675 | 0.001194 | 1.70E−05 |
| MEOH | 0.574541 | 0.994661 | 0.002354 |
| PGME | 0.226784 | 0.004145 | 0.997629 |
| Liq Vol 60F l/min | | | |
| PO | 11.66402 | 0.032696 | 0.000532 |
| MEOH | 34.95619 | 28.2301 | 0.0764 |
| PGME | 11.94976 | 0.101884 | 28.04569 |
| LiqVolFrac60F | | | |
| PO | 0.199147 | 0.001153 | 1.89E−05 |
| MEOH | 0.596828 | 0.995255 | 0.002717 |
| PGME | 0.204025 | 0.003592 | 0.997264 |

TABLE 9

Stage profile for the CD1 column.

| Stage | Temperature C | Pressure Atm | Heat duty kJ/hr | Liquid flow kg/hr | Vapor flow kg/hr | Liquid feed kg/hr |
|---|---|---|---|---|---|---|
| 1 | 89.80245 | 2.5 | −3511269 | 2029.195 | 0 | 0 |
| 2 | 90.06343 | 2.5 | 0 | 2039.383 | 3381.99159 | 0 |
| 3 | 90.71838 | 2.5 | 0 | 2071.654 | 3392.17935 | 0 |
| 4 | 92.48858 | 2.5 | 0 | 2130.609 | 3424.45068 | 0 |
| 5 | 96.0632 | 2.5 | 0 | 2124.458 | 3483.40589 | 0 |
| 6 | 99.39895 | 2.5 | 0 | 4950.726 | 3427.75824 | 2850.504 |
| 7 | 112.8926 | 2.5 | 0 | 6117.854 | 3403.52215 | 0 |
| 8 | 133.6004 | 2.5 | 0 | 7523.34 | 4570.65042 | 0 |
| 9 | 146.7346 | 2.5 | 0 | 8398.535 | 5976.13684 | 0 |
| 10 | 150.9134 | 2.5 | 2918085 | 1547.203 | 6851.3313 | 0 |

Lower Capital Investment and Energy Consumption with CD Processes

Energy Consumption Comparison

Table 10 summarizes the energy consumption for the three processes used to produce PGME. In Case 1, the traditional process for a liquid phase reactor requires cooling duty in order to maintain the reactor at 100° C. This heat is integrated into the CD column and therefore the overall heating and cooling requirement of the new process is lower (Case 2). It can be seen from Table 10 that by converting the traditional process (Case 1) to the catalytic distillation processes (Cases 2 and 3); the savings in cooling water and steam are in excess of 30%. Even in Case 3, where a prereactor is used before the CD column, advantages may be realized. Since the prereactor is allowed to operate adiabatically, no additional heating or cooling is required. Although the heating and cooling duties of the CD column are slightly higher than in Case 2, the savings are realized in the form of lower capital and operating costs.

TABLE 10

Summary of energy consumption in Cases 1-3

| | Cooling duty (kJ/hr) | | | Steam duty (kJ/hr) |
|---|---|---|---|---|
| Case/ Example | Reactor | Distillation/ CD column | Total Cooling Duty | Distillation/CD column |
| 1 | −784836 | −4433808 | −5218644 | 4327372 |
| 2.1 | None | −3464863 | −3464863 | 2878747 |
| 2.2 | None | −3464913 | −3464913 | 2878928 |
| 3.1 | None | −3511452 | −3511452 | 2917515 |
| 3.2 | None | −3511269 | −3511269 | 2918085 |

Capital Cost Comparison

The largest pieces of equipment in the process, namely the reactor and separation column, have a significant impact on the overall capital cost. Since they make up the largest costs, any reduction in the number of pieces of equipment or size of the column could be a potential for savings. Comparing Case 1 and Case 2, Case 1 has more pieces of equipment, namely a reactor, a distillation column and associated heat exchangers. As well, Case 1 also requires a cooling system for controlling the temperature of the reactor. In Case 2 all of the operations have been combined into one unit, the CD column. In Case 2, which only requires a single CD column, 10 to 20 stages are required to achieve the desired reaction and separation of the PGME product (Table 4). However, we have optimized for 20 stages (it is possible to use stages in the range of 10 to 20 stages if other parameters are also varied).

In comparison, Case 3 where a prereactor has been added to the process, the number of stages in CD column 150 is optimally reduced from 20 to 10 stages (Table 7), but it could also be less than 10. This could offer a substantial savings in the construction of the CD column. As well, this distinction is independent of which catalyst system is used. Whether a heterogeneous catalyst (compare cases 2.1 and 2.2) or a dual heterogeneous/homogeneous catalyst system is used (compare cases 3.1 and 3.2) the stages required for separation remain the same and the capital costs would be similar.

REFERENCES

1. Chitwood, H. C., and Freure, B. T., JACS, Vol. 68, Iss. 4, 1946.
2. Reeve, W. and Sadie, A., JACS, Vol. 72, Iss. 3, 1950.
3. Pecorini, H. A., and Banchero, J. T., IndEngChem, Vol. 48, Iss. 8, 1956.

The invention claimed is:

1. A process for producing propylene glycol methyl ether, comprising
    (a) dissolving a solid basic catalyst in methanol to form a homogeneous solution,
    (b) feeding the solution to a catalytic distillation column containing a heterogeneous basic catalyst fixed in place in the column, defining a heterogeneous reaction zone, wherein the heterogeneous basic catalyst is an anion exchange resin in free base form selected from weak anionic resins based on a macroporous, cross-linked, styrene divinyl benzene polymer structure having a tertiary amine functionality
    (c) feeding propylene oxide to the column, wherein, in the column, methanol reacts with propylene oxide according to a dual homogeneous catalytic reaction and heterogeneous catalytic reaction to form propylene glycol methyl ether, and
    (d) removing substantially pure propylene glycol methyl ether from the column as a bottoms product.

2. The process of claim 1, wherein the homogeneous basic catalyst is anhydrous sodium methoxide or potassium methoxide.

3. The process of claim 2, wherein the pressure in the catalytic distillation column is 1.8 to 4 atm.

4. The process of claim 3, wherein the pressure in the catalytic distillation column is about 3 atm.

5. The process of claim 4, wherein the molar feed ratio of methanol to propylene oxide to the catalytic distillation column is 1.5 to 5.

6. The process of claim 5, wherein the temperature in the heterogeneous reaction zone in the catalytic distillation column is maintained at about 70 to 100° C., and the temperatures above and below the heterogeneous reaction zone are in the range of 50 to 70° C. and 100 to 160° C., respectively.

7. The process of claim 6, wherein the catalytic distillation column includes a plurality of numbered stages arranged numerically from top to bottom, and the homogeneous catalyst/methanol solution is fed to the column near the top and the propylene oxide is fed to the column near the bottom.

8. The process of claim 7, wherein the catalytic distillation column includes 10-20 stages.

9. The process of claim 8, wherein the catalytic distillation column includes 20 stages.

10. The process of claim 9, wherein the catalytic distillation column includes stages numbered 1 to 20, the heterogeneous catalyst is located at stages 4 to 7, the homogeneous solution is fed to the column at stage 2, and the propylene oxide is fed to the column either as a single feed stream at stage 9, or as multiple feed streams on any of the stages within the heterogeneous reaction zone.

11. The process of claim 10, wherein the molar feed ratio is about 3.44.

12. The process of claim 11, wherein the amount of heterogeneous catalyst in the catalytic distillation column is 150 to 500 kg per 1000 kg/h of propylene oxide feed, and the amount of homogeneous catalyst in the methanol feed is in the range of 0.001 to 0.01 of the weight of the heterogeneous catalyst used.

13. The process of claim 2, wherein the homogeneous catalyst in methanol solution and propylene oxide are first fed to a liquid phase pre-reactor, which is in fluid communication with the catalytic distillation column, the pre-reactor containing a basic heterogeneous catalyst fixed in place therein for reacting, and methanol with propylene oxide according to a dual homogeneous catalytic reaction and heterogeneous catalytic reaction to form propylene glycol methyl ether, and when the temperature in the pre-reactor reaches about 100° C., transferring the reaction products so formed to the catalytic distillation column for further reaction.

14. The process of claim 13, wherein the catalytic distillation column includes ten stages numbered 1 to 10 from top to bottom, and wherein the heterogeneous catalyst is located at stages 2 to 6, and wherein the homogeneous reaction occurs at stage 6, ie., where the reaction products from the pre-reactor are fed into the catalytic distillation column.

15. The process of claim 14, wherein the pressure in the catalytic distillation column is about 2.5 atm and the pressure in the pre-reactor is about 0.2 to 0.5 atm higher than that in the catalytic distillation column.

16. A process is provided for producing propylene glycol methyl ether comprising
    (a) dissolving a solid basic catalyst in methanol to form a homogeneous solution,
    (b) feeding the solution to a liquid phase pre-reactor containing a heterogeneous basic catalyst fixed in place therein, operating adiabatically,
    (c) feeding propylene oxide to the pre-reactor-containing a heterogeneous basic catalyst, wherein the heterogeneous basic catalyst is an anion exchange resin in free base form selected from weak anionic resins based on a macroporous, cross-linked, styrene divinyl benzene olymer structure having a tertiary amine functionality fixed in place in the pre-reactor, operating adiabatically, wherein methanol reacts with propylene oxide according to a dual homogeneous catalytic reaction and heterogeneous catalytic reaction to form propylene glycol methyl ether, and when the temperature in the pre-reactor reaches about 100° C., transferring the reaction products so formed to a catalytic distillation column containing the heterogeneous basic catalyst fixed in place therein defining a heterogeneous reaction zone, and where additional methanol may be added to a catalytic distillation column for further reaction, and where additional methanol may be added to the catalytic distillation column for further reaction, and
    (d) removing substantially pure propylene glycol methyl ether from the column as a bottoms product.

17. The process of claim 16, wherein the homogeneous basic catalyst is anhydrous sodium methoxide or potassium methoxide.

18. The process of claim 17, wherein the pressure in the catalytic distillation column is 1.8 to 4 atm and wherein the molar feed ratio of methanol to propylene oxide to the catalytic distillation column is 1.5 to 5.

19. The process of claim 18, wherein the catalytic distillation column includes ten stages numbered 1 to 10 from top to bottom, and wherein the heterogeneous catalyst is located at stages 2 to 6, and wherein the homogeneous reaction occurs at stage 6 ie. where the reaction products from the pre-reactor are fed into the catalytic distillation column and wherein the pressure in the catalytic distillation column is about 2.5 atm and the pressure in the pre-reactor is about 0.2 to 0.5 atm higher than that in the catalytic distillation column.

20. The process of claim 1, wherein the anion exchange resin has the formula

21. The process of claim 16, wherein the anion exchange resin has the formula

* * * * *